US00PP09332P

United States Patent [19]

Zaiger et al.

[11] Patent Number: Plant 9,332

[45] Date of Patent: Oct. 17, 1995

[54] NECTARINE TREE "ARCTIC STAR"

[76] Inventors: Chris F. Zaiger, 929 Grimes Ave.; Gary N. Zaiger, 1907, Elm Ave.; Leith M. Gardner, 1207 Grimes Ave.; Grant G. Zaiger, 4005 California Ave., all of Modesto, Calif. 95358

[21] Appl. No.: 364,802

[22] Filed: Dec. 27, 1994

[51] Int. Cl.[6] ..... A01H 5/00

[52] U.S. Cl. ..... Plt./40.1

[58] Field of Search ..... Plt./40.1

*Primary Examiner*—James R. Feyrer

[57] ABSTRACT

A new and distinct variety of nectarine tree which has the unique combination of the following outstanding features that are desirable in a new variety:

1. Fruit with good flavor and eating quality.
2. Heavy and regular production of fruit.
3. Fruit having firm white flesh with good handling and shipping quality.
4. Fruit with a high degree of attractive red skin color.
5. Vigorous, upright growth.
6. Relatively uniform size of fruit throughout the tree.

1 Drawing Sheet

ORIGIN OF THE VARIETY

The present new variety of nectarine tree was originated by use in our experimental orchard located near Modesto, Calif., as a first generation cross between a white nectarine of unknown parentage and May Glo Nectarine (U.S. Plant Pat. No. 5,245). A large number of seedlings from this first generation cross were planted, grown and maintained under careful observation, during which time one such seedling, which represents the present variety, being especially desirable for the quality of its fruit, was selected for asexual reproduction and commercialization.

ASEXUAL REPRODUCTION OF THE VARIETY

Asexual reproduction of the new and distinct variety of nectarine tree was reproduced by budding, as performed by us in our experimental orchard located near Modesto, Calif., which shows that all characteristics of the tree and its fruit are established and transmitted through succeeding asexual propagations and are true to the original tree in all respects.

SUMMARY OF THE VARIETY

The herein claimed new distinct variety of nectarine tree is of large size, vigorous, upright growth and is a productive and regular bearer of large size, white flesh, clingstone fruit with good flavor and eating quality. The fruit is further characterized by having firm white flesh, good storage and handling quality and having a high degree of attractive red skin color. In comparison to its low chill pollen parent May Glo Nectarine (U.S. Plant Pat. No. 5,245), the new variety requires approximately 150 more winter chilling hours, produces fruit that is larger in size, has white flesh instead of yellow flesh and is approximately 3 days later in maturity.

DESCRIPTION OF THE PHOTOGRAPHS

The accompanying color photographic reproductions show typical specimens of the foliage and fruit of the present new nectarine variety. The illustrations are of the upper and lower surface of the leaves, and of the exterior and sectional view of the fruit divided in its suture plane to reveal the pit cavity, flesh coloration and a stone remaining in place. The photographs were taken shortly after the fruit was picked (firm ripe) and the colors are as nearly true as is reasonably possible in a color representation of this type.

DESCRIPTION OF THE VARIETY

The following is a detailed botanical description of the present new variety of nectarine tree, its flowers, foliage and fruit as based on observations of specimens grown near Modesto, Calif., with color terminology (except those in common terms) referenced to Reinhold Color Atlas by A. Kornerup and J. H. Wanscher.

Tree:
- *Size.*—Large.
- *Vigor.*—Vigorous.
- *Form.*—Upright.
- *Density.*—Medium dense.
- *Productivity.*—Productive.
- *Bearing.*—Regular.

Trunk:
- *Size.*—Medium to large.
- *Texture.*—Medium shaggy.
- *Color.*—Brown to soot brown (5-E-5) to (5-F-5).

Branches:
- *Size.*—Medium.
- *Texture.*—Medium rough.
- *Lenticels.*—Numerous. Medium to large size.
- *Color.*—Light brown to oak brown (5-D-5) to (5-D-6).

Leaves:
- *Size.*—Large. Average length — 6½". Average width — 1⅝".
- *Texture.*—Smooth.
- *Margin.*—Crenate.
- *Form.*—Lanceolate. Pointed.
- *Thickness.*—Medium.
- *Petiole.*—Medium length. Medium thickness
- *Glands.*—Reinform. Small to medium size. Number varies from 1 to 4. Average number 2. Positioned on base of leaf blade and upper portion of petiole.
- *Color.*—Upper surface — light green to green (28-E-8) to (28-F-5). Lower surface — dull green to grayish green (28-D-5) to (28-E-5).

Flower buds:
- *Size.*—Medium to large.
- *Length.*—Medium.
- *Form.*—Plump — free.

Flowers:
- *Size.*—Large — showy.
- *Blooming period.*—Date of first bloom — Feb. 16, 1993. Date of full bloom — Feb. 20, 1993. Varies slightly with climatic conditions.
- *Pollen.*—Present — self fertile.
- *Color.*—Pink.

*Pistil pubescence.*—Wanting.

Fruit:

*Maturity when described.*—Firm ripe.

*Date of first picking.*—May 30, 1993.

*Date of last picking.*—Jun. 6, 1993. Maturity varies slightly with climatic conditions.

*Size.*—Medium to large. Average diameter axially — Average transversely in suture plane — 2 11/16".

*Form.*—Globose — nearly symmetrical.

*Suture.*—Shallow — extends from base to apex.

*Ventral surface.*—Nearly rounded, varies from round to slight depression.

*Base.*—Retuse.

*Apex.*—Usually rounded, varies from retuse to slight pistil point.

*Cavity.*—Rounded to slightly elongated in suture plane. Average depth — 7/16". Average breadth — 5/8".

Flesh:

*Ripens.*—Uniform.

*Texture.*—Firm, meaty.

*Fibers.*—Few, small, tender.

*Juice.*—Moderate.

*Flavor.*—Good, subacid to mild.

*Eating quality.*—Good.

*Aroma.*—Moderate.

*Color.*—White to yellowish white (2-A-1) to (2-A-2). Pit cavity — cream white to yellowish white. (4-A-2) to (4-A-3).

Skin:

*Thickness.*—Medium.

*Texture.*—Medium — tenacious to the flesh.

*Tendency to crack.*—None.

*Down.*—Wanting.

*Color.*—White ground color (2-A-1) to (2-A-2). Overspread with red (10-C-8) to (10-D-8).

Stone:

*Type.*—Clingstone.

*Size.*—Large. Average length — 1¼". Average width — 1". Average thickness — ½".

*Form.*—Ovoid.

*Base.*—Varies from straight to rounded.

*Apex.*—Acuminate.

*Sides.*—Equal to slightly unequal.

*Surface.*—Furrowed toward apex, pitted toward base.

*Ridges.*—Rounded.

*Tendency to split.*—Very slight.

*Color.*—Light brown to brown (8-B-5) to (8-D-5).

Use: Dessert.

*Market.*—Local and long distance.

Keeping quality: Good.

Shipping quality: Good.

The present new variety of nectarine tree, its flowers, foliage and fruit herein described may vary in slight detail due to climate, soil conditions and cultural practices under which the variety may be grown. The present description is that of the variety grown under the ecological conditions prevailing near Modesto, Calif.

We claim:

1. A new and distinct variety of nectarine tree, substantially as illustrated and described, characterized by its large size, vigorous upright growth, which is a productive and regular bearer of large, early maturing, white flesh clingstone fruit with good flavor and eating quality; the fruit is further characterized by having firm flesh with good storage and shipping quality, having a high degree of attractive red skin color and in comparison to its paternal parent May Glo Nectarine (U.S. Plant Pat. No. 5,245) it has white flesh instead of yellow flesh, is slightly larger in size and is approximately 3 days later in maturity.

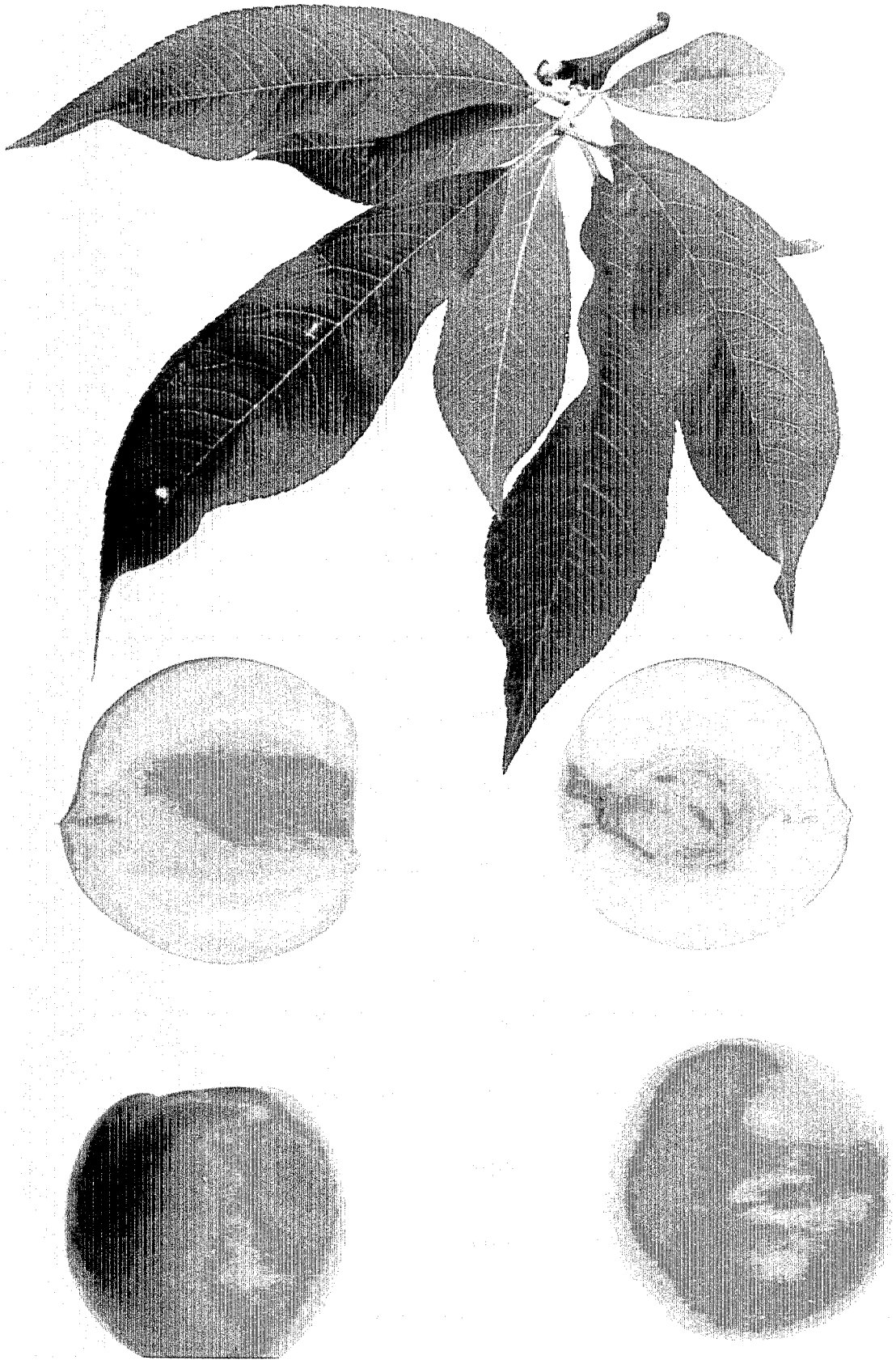

* * * * *